US006615433B2

(12) United States Patent
Crevasse et al.

(10) Patent No.: US 6,615,433 B2
(45) Date of Patent: Sep. 9, 2003

(54) APPARATUS FOR DETECTING WETNESS OF A SEMICONDUCTOR WAFER CLEANING BRUSH

(75) Inventors: Annette M. Crevasse, Apopka, FL (US); William G. Easter, Orlando, FL (US); John A. Maze, Orlando, FL (US); Frank Miceli, Orlando, FL (US)

(73) Assignee: Agere Systems Inc., Allentown, PA (US)

( * ) Notice: Subject to any disclaimer, the term of this patent is extended or adjusted under 35 U.S.C. 154(b) by 0 days.

(21) Appl. No.: 09/821,506

(22) Filed: Mar. 29, 2001

(65) Prior Publication Data

US 2002/0139393 A1 Oct. 3, 2002

(51) Int. Cl.[7] .............................. B08B 1/02; B08B 1/04
(52) U.S. Cl. .............................. 15/77; 15/88.3; 15/102
(58) Field of Search .................... 15/77, 88.2, 88.3, 15/102

(56) References Cited

U.S. PATENT DOCUMENTS

| | | | | |
|---|---|---|---|---|
| 4,382,308 A | * | 5/1983 | Curcio | ............................ 15/77 |
| 5,007,335 A | * | 4/1991 | Orman et al. | .................. 99/487 |
| 5,012,526 A | * | 5/1991 | Romans et al. | .......... 15/88.3 X |
| 5,095,926 A | * | 3/1992 | Wegner | .................... 15/88.3 X |
| 6,269,510 B1 | * | 8/2001 | Beardsley et al. | ............. 15/77 |

* cited by examiner

*Primary Examiner*—Mark Spisich

(57) ABSTRACT

The present invention provides a wafer cleaning apparatus. In an advantageous embodiment, the wafer cleaning apparatus includes cleaning brushes mounted within a brush box and a sensor associated with at least one of the cleaning brushes and configured to detect a degree of wetness of the at least one of the cleaning brushes. In most cases, the cleaning brushes are comprised of an absorbent material, such as polyvinyl alcohol, that becomes more compressible as the cleaning brushes become more wetted with a solution. Thus, a degree of compressibility can be related to a degree of wetness of a cleaning brush, which provides data that allows an operator to determine when the cleaning brushes are wet enough to send a wafer through the cleaning apparatus without incurring unnecessary damage.

7 Claims, 4 Drawing Sheets

APPARATUS FOR DETECTING WETNESS OF A SEMICONDUCTOR WAFER CLEANING BRUSH

TECHNICAL FIELD OF THE INVENTION

The present invention is directed, in general, to cleaning semiconductor wafers and, more specifically, to an apparatus and method for detecting the wetness of a semiconductor wafer cleaning brush.

BACKGROUND OF THE INVENTION

During semiconductor manufacturing, several processes create debris that must be removed from the semiconductor wafers to prevent any contamination of the integrated circuits (ICs) derived from the wafers. Some of the processes well known for depositing contaminating particles on the surface of semiconductor wafers are silicon polishing, laser scribing and chemical/mechanical polishing.

Silicon polishing is performed after a silicon ingot is cut into wafers to prepare the wafers for further precessing. Laser scribing is the process by which identifying numbers are scribed into the wafer, and chemical-mechanical polishing uses an abrasive slurry to planarize the wafer surface. Each of these processes creates debris that may cling to the wafer surface and present a potential contamination hazard. The most common particles left after such processes include tungsten, titanium, titanium nitride, aluminum, tantalum, polishing pad particles and slurry particles. With the high cost of semiconductor manufacturing and intense competition among manufacturers, every effort must be made to minimize the contamination hazard presented by one or more of these particles.

Thus, for reasons of both thoroughness and efficiency, these contaminants are perhaps best removed from the wafer surface by mechanical means. In a typical wafer cleaning apparatus, the surfaces of the semiconductor wafer are best cleaned of any residual debris by passing the wafer through a cleaning box having multiple rollers equipped with cleaning brushes rotating within. While in use, the combination of brush rotation and pressure applied to the semiconductor wafer through the brushes provides for the proper cleaning of the semiconductor wafer surfaces.

The cleaning brushes found in the cleaning box are usually constructed of polyvinyl alcohol (PVA) or a material having similar properties. Among these properties are the tendency of the cleaning brush to remain very hard when dry, but soft and spongy when kept wetted. Ammonium hydroxide or diluted hydrofluoric acid are common cleaning solutions used to wet the brushes while cleaning semiconductor wafers. In addition, the cleaning brushes may also be kept wetted with de-ionized water to maintain the soft, spongy surface found on wetted brushes when a cleaning solution is not needed.

However, a recurring problem in the art is the cleaning of a wafer with a drying or dried cleaning brush. This problem may occur when a new cleaning brush has been installed or when the cleaning apparatus is first used after a long respite where the cleaning brushes have been allowed to dry. Additionally, this problem may occur while the cleaning apparatus is in used if the brushes are not sufficiently wetted throughout the cleaning process. Since typical cleaning brushes used for semiconductor wafer cleaning become harder as they dry, significant damage to the surface of the wafers passed through a cleaning box with dry brushes may occur. Specifically, a dry, hard cleaning brush will easily scratch the surface of a wafer, often times damaging the integrated circuits (ICs) to be derived from the wafer. Sometimes the damage to the wafer is so extensive the entire wafer must be discarded. Thus, with the high cost of materials in the competitive semiconductor market, manufacturers cannot afford to risk passing a wafer through a cleaning apparatus without first being certain the cleaning brushes are adequately wetted.

Prior art efforts to determine if the brushes in a cleaning apparatus are sufficiently wetted before a semiconductor wafer is passed through have generally been inadequate. At first glance, an obvious solution would be to overly inundate the cleaning brushes with cleaning solution prior to and during the cleaning process. Of course, the expense of wasted cleaning solution leads most manufacturers to shy away from this approach. Another approach has been to put windows in the sides of the cleaning apparatus so that the brushes may be visually inspected before the cleaning process. Unfortunately, the most common cleaning solutions used in the industry are negatively effected by exposure to light. In some cases, exposure to light may even result in a chemical reaction in the cleaning solution decreasing its potency.

Another attempt to overcome the problem of dry cleaning brushes has been to incorporate a flow sensor into the chemical dispensing system of the cleaning apparatus. However, this approach is also often unsuccessful since it only informs the operator that a fluid is flowing through the dispensing system, but not whether the cleaning brushes have been sufficiently wetted by that fluid or even what type of fluid is being dispensed. Even if this approach is successful in guessing that the brushes are sufficiently wetted, there is no guarantee that the brushes will remain sufficiently wetted from one wafer to the next, throughout the cleaning process. Moreover, knowing whether a harmful solution rather than simply de-ionized water has flowed through the cleaning apparatus can be very helpful to prevent the risk of burning a technician who must open the apparatus to perform maintenance.

Yet another approach has been to physically open the cleaning apparatus to visually inspect the saturation of the cleaning brushes. One disadvantage to this approach is the time necessary for the technician to open the cleaning apparatus, make the inspection and then reseal the apparatus. A more serious concern is the risk of the technician being burned by any cleaning solutions present within the apparatus when opened. Of course, most manufacturers would like to avoid placing their technicians or other personnel at risk of being chemically burned by the cleaning solutions used during the cleaning process.

Accordingly, what is needed in the art is an effective technique for determining whether the cleaning brushes in a semiconductor wafer cleaning apparatus are sufficiently wetted with cleaning solution, before wafers are pass through the apparatus, that does not suffer from the deficiencies found in the prior art.

SUMMARY OF THE INVENTION

To address the above-discussed deficiencies of the prior art, the present invention provides a wafer cleaning apparatus. In an advantageous embodiment, the wafer cleaning apparatus includes cleaning brushes mounted within a brush box and a sensor associated with at least one of the cleaning brushes and configured to detect a degree of wetness of the at least one of the cleaning brushes. The sensor includes a number of configurations as discussed in detail below. For example, the sensor may be a compressibility sensor that is configured to detect the amount of force required to compress the cleaning brush. In most cases, the cleaning brushes are comprised of an absorbent material, such as polyvinyl alcohol, that becomes more compressible as the cleaning brushes become more wetted with a solution. Thus, a degree of compressibility can be related to a degree of wetness of a cleaning brush, which provides data that allows an operator to determine when the cleaning brushes are wet enough to send a wafer through the cleaning apparatus without incurring unnecessary damage.

Other embodiments include pressure sensors, optical sensors, torque sensors, pH sensor, humidity sensors, and acoustic sensors, all of which can be designed, i.e. configured, to detect a change in the amount of wetness of the cleaning brush.

The foregoing has outlined, rather broadly, preferred and alternative features of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention. Those skilled in the art should also realize that such equivalent constructions do not depart from the spirit and scope of the invention in its broadest form.

BRIEF DESCRIPTION OF THE DRAWINGS

For a more complete understanding of the present invention, reference is now made to the following descriptions taken in conjunction with the accompanying drawings, in which.

DETAILED DESCRIPTION

Figure 1:
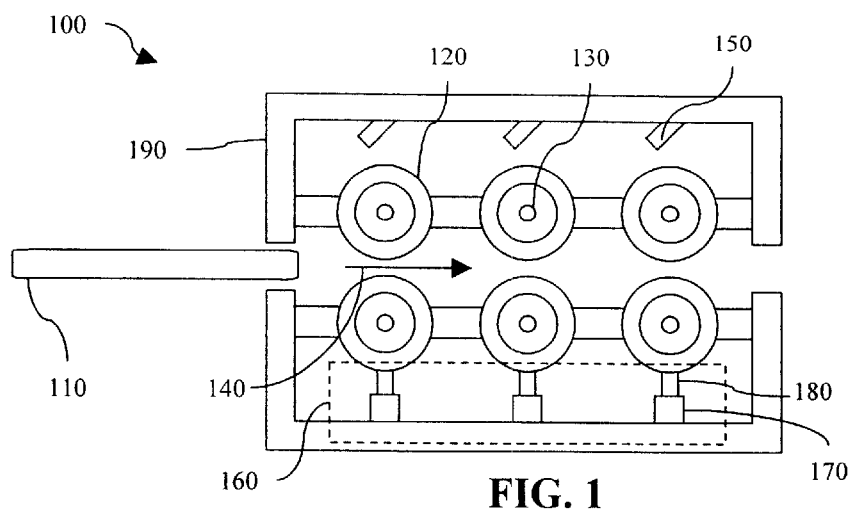
FIG. 1 illustrates a side, sectional view of a semiconductor wafer cleaning apparatus incorporating one embodiment of a detection system manufactured according to the principles of the present invention.

Referring initially to FIG. 1, illustrated is a side, sectional view of a semiconductor wafer cleaning apparatus 100 incorporating one embodiment of a detection system 160 manufactured according to the principles of the present invention. As illustrated, the cleaning apparatus 100 includes a brush box 190 having six cleaning brushes 120 for cleaning a substrate 110, such as a semiconductor wafer. Although only six brushes 120 are illustrated, it must be noted that no embodiment of the present invention is limited to any particular number of cleaning brushes 120.

The cleaning brushes 120 used in the cleaning operation are typically constructed of an absorbent material, such as polyvinyl alcohol (PVA). Since the cleaning brushes 120 are composed of an absorbent material, they also typically have an increasing compressibility as they become wetted with a wetting solution. More specifically, the cleaning brushes 120 have a predetermined compressibility when thoroughly wetted with a cleaning solution, with the compressibility decreasing as the cleaning brush 120 dries. Consequently, when the cleaning brush 120 completely dries, it is usually quite hard and can easily scratch the surface of the substrate 110 if used in this dry state. Scratching of the surface may result in many of the integrated circuits (ICs) to be derived from the substrate 110 being defective. In fact, if such scratching is too extensive or severe, the damage to the substrate 110 is likely irreparable resulting in the substrate 110 having to be discarded.

Those skilled in the art understand that the likelihood of scratching the substrate 110 during the cleaning process decreases as the cleaning brushes 120 attain a higher degree of wetness. Thus, it is extremely beneficial for the operator of the cleaning apparatus 100 to be certain the cleaning brushes 120 have a high degree of wetness before the substrate 110 is passed through the brush box 190. Through the relationship between the compressibility and wetness of a cleaning brush 120, the risk of damage to the substrate 110 during the cleaning process may be determined by detecting the degree of wetness of the cleaning brush 120.

The cleaning apparatus 100 further includes dispensers, one of which is designated 150, for dispensing the cleaning solution on the cleaning brushes 120 prior to a cleaning process. During the cleaning process, the substrate 110 is fed into the brush box 190, and between the cleaning brushes 120, along a longitudinal path 140. Once inside, the cleaning brushes 120 are rotated about respective shafts 130 and come in contact with the surfaces of the substrate 110 to be cleaned. As the substrate 110 passes through the cleaning apparatus 100, the substrate 110 is compressed between opposing cleaning brushes 120. As such, the cleaning brushes 120 must be sufficiently wetted, and consequently compressible, so as to not damage the substrate 110 as it passes through the cleaning apparatus 100.

To ensure the cleaning brushes 120 are sufficiently wetted, this embodiment of the detection system 160 includes multiple pH sensors, one of which is designated 170. Each pH sensor 170 includes its own sensing probe 180 for determining the pH level of at least one of the cleaning brushes 120. Since pH detection is a direct measurement of the concentration of hydrogen ions, by measuring the pH level of a cleaning brush 120, the detection system 160 can determine the concentration of cleaning solution, which is usually composed of ammonium hydroxide or hydrofluoric acid. A predetermined pH level determined by the detection system 160 would then indicate to an operator that the cleaning brush 120 is wetted with a sufficient concentration of cleaning solution before the cleaning process is started. Specifically, since the cleaning solution has a given pH level, when the detection system 160 detects that pH level on the cleaning brush 120, the cleaning brush 120 can be said to be sufficiently wetted. Conversely, if the cleaning brush 120 is only sparsely moistened, the detection system 160 will detect a pH level lower than that of pure cleaning solution, thus the operator will be informed that the cleaning brush 120 is not sufficiently wetted with the solution before the cleaning process. When the detection system 160 makes this determination, it may be configured to transmit a signal to the operator of the cleaning apparatus 100 verifying the degree of wetness of the cleaning brushes 120.

By determining the cleaning brushes 120 have at least a minimum pH level before the substrate 110 is cleaned, the detection system 160 of the present invention prevents damage that may occur when using a cleaning brush 120 which is not sufficiently wetted. Moreover, the detection system 160 achieves this goal while overcoming deficiencies of the approaches found in the prior art. Specifically, the detection system 160 makes the determination of wetness, and consequently compressibility, without the delay of having to open the cleaning apparatus 100 to visually inspect the cleaning brushes 120 or unnecessarily delaying the cleaning process because the operator is forced to simply allow the dispensers 150 to spray solution for a prolonged period rather than guess whether the cleaning brushes 120 have been sufficiently wetted and prematurely begin the cleaning process.

In addition, in this embodiment of the present invention the detection system 160 further provides a useful safety device for technicians needing to open the cleaning apparatus 100 to perform maintenance. For example, if one or more cleaning brushes 120 require replacement, a technician may want to ensure that no harmful chemicals are present on the cleaning brush 120 when he handles it. Persons familiar with the process of cleaning a semiconductor substrate 110 are aware of the risk of chemical burns when working in the presence of many of the commonly used cleaning solutions. While de-ionized water is safe for a technician to come in contact with, hydrofluoric acid is an extremely hazardous chemical capable of causing severe injuries. To help alleviate this risk, the detection system 160 may be employed to alert the technician to the presence of any harmful cleaning solutions in the cleaning apparatus 100 before it is opened by simply determining the pH level present in any one or more of the cleaning brushes 120. If cleaning solution is found, the technician may then thoroughly rinse the brush box 190 and cleaning brushes 120 again before opening it and risking exposure to harmful chemicals.

Figure 2:
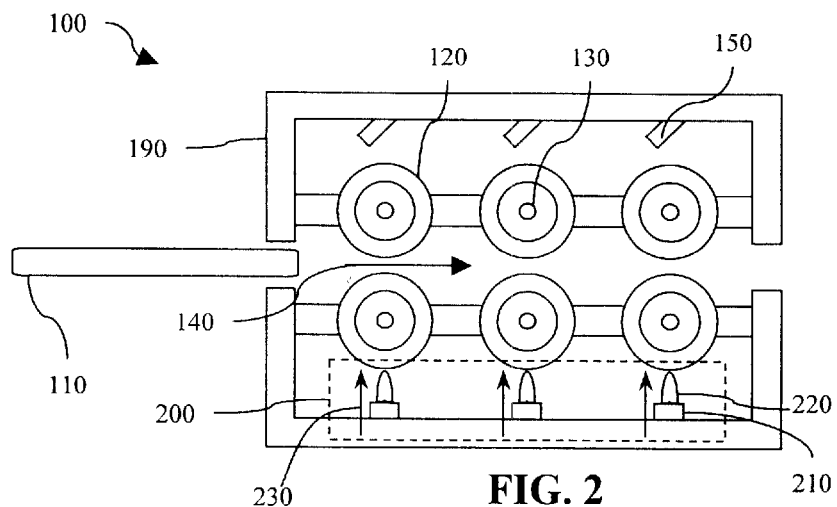
FIG. 2 illustrates a side, sectional view of the cleaning apparatus of FIG. 1 incorporating another embodiment of a detection system of the present invention.

Turning now to FIG. 2, illustrated is a side, sectional view of the cleaning apparatus 100 of FIG. 1 incorporating another embodiment of a detection system 200 of the present invention. The cleaning apparatus 100 still includes the brush box 190 having the cleaning brushes 120 rotated on shafts 130 and wetted with cleaning solution by the dispensers 150. As before, the substrate 110 is fed into the cleaning apparatus 100 along a longitudinal path 140 and passed between opposing cleaning brushes 120.

Rather than a pH level detector, the detection system 200 of FIG. 2 now includes compressibility sensors, one of which is designated 210. Each cleaning brush 120 is illustrated having its own compressibility sensor 210, however the present invention is not limited to a particular number of compressibility sensor 210. Each of the compressibility sensors 210 includes an extendable member, one of which is designated 220. This embodiment of the detection system 200 functions as follows.

As discussed above, the compressibility of the cleaning brushes 120 increases as they are wetted with the cleaning solution until the cleaning brushes 120 have sufficient wetness and compressibility to clean the substrate 110 without damaging it. To detect when the cleaning brushes 120 have this predetermined degree of wetness the extendable members 220 of the compressibility sensors 210 project in an outward direction 230, towards the cleaning brushes 120. As the extendable members 220 contact and press against the cleaning brushes 120 they are able to detect the amount of compressibility present. When the compressibility sensors 210 detect that the predetermined amount of compressibility is present in the cleaning brushes 120, a signal may be sent to inform the operator that the substrate 110 may be safely fed through the cleaning apparatus 100 since the risk of damage to the substrate's 110 surface has been reduced or eliminated. As with the embodiment of FIG. 1, the detection system 200 provides this information without suffering from the delays or risks associated with the approaches found in the prior art.

Figure 3:
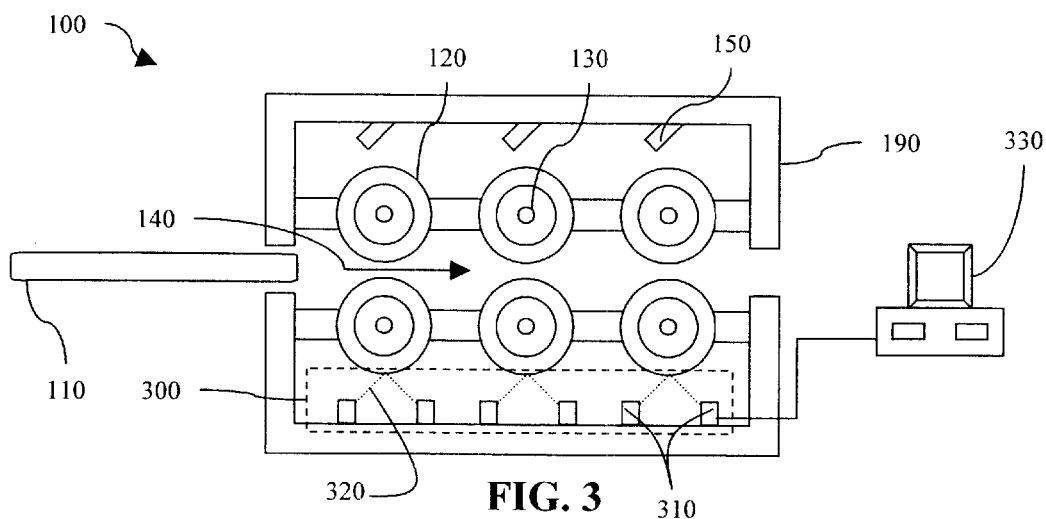
FIG. 3 illustrates a side, sectional view of the cleaning apparatus of FIG. 1 incorporating a further embodiment of a detection system.

Now referring to FIG. 3, illustrated is a side, sectional view of the cleaning apparatus 100 of FIG. 1 incorporating a further embodiment of a detection system 300 of the present invention. The cleaning apparatus 100 still includes the brush box 190, cleaning brushes 120, shafts 130 and dispensers 150 collectively used for cleaning the substrate 110.

In this embodiment of the present invention, the detection system 300 includes optical sensors, one pair of which are designated 310. The optical sensors 310 work in pairs and provide a particle beam 320 between any two sensors 310, reflected off of the surface of the cleaning brush 120. The degree of reflectivity detected by the optical sensors 310 determine the amount of cleaning solution present in, and consequently the degree of wetness of, the cleaning brush 120. More specifically, it has been found that the particle beam 320 will easily reflect off of the surface of a cleaning brush 120 having a high degree of wetness, while having greater difficulty reflecting off of the surface of a cleaning brush 120 with a low degree of wetness. Based on these properties, each pair of optical sensors 310 in the detection system 300 is configured to attempt to bounce a particle beam 320 off of a particular cleaning brush 120 in order to determine its degree of wetness.

Depending on the difficulty, or perhaps the inability, of the particle beam 320 to reflect off of the cleaning brush 120, the amount of cleaning solution present in the cleaning brush 120, and thus the degree of wetness, is detected. As discussed above, the degree of wetness of the cleaning brush 120, in turn, gives an accurate determination of the amount of compressibility of the cleaning brush 120. By configuring the optical sensors 310 to transmit a signal to a computer system 330 when a predetermined degree of wetness of the cleaning brush 120 is detected, the detection system 300 of FIG. 3 allows an operator to use the computer system 330 to determine whether to proceed with the cleaning process confident that the substrate will not be inadvertently damaged. Moreover, the detection system 300 provides this confidence to proceed with the cleaning process without the deficiencies found in prior art approaches.

Figure 4:
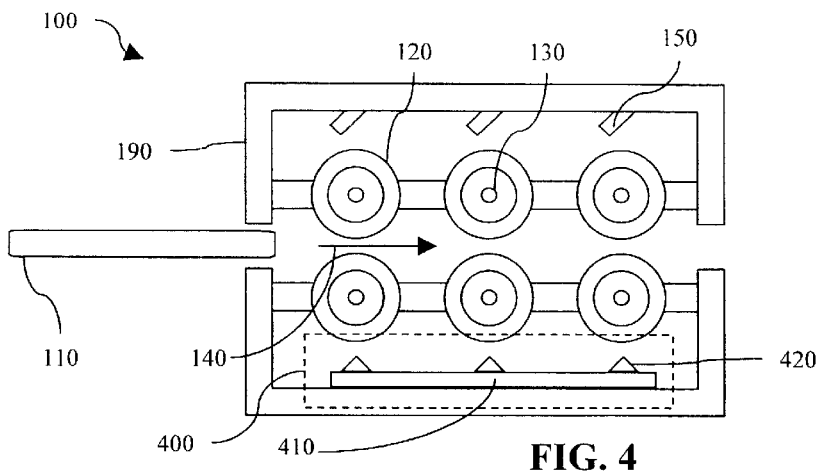
FIG. 4 illustrates a side, sectional view of the cleaning apparatus of FIG. 1 incorporating still another embodiment of a detection system.

Now turning to FIG. 4, illustrated is a side, sectional view of the cleaning apparatus 100 of FIG. 1 incorporating still another embodiment of a detection system 400 of the present invention. Again, the cleaning apparatus 100 includes the brush box 190 having the cleaning brushes 120, the shafts 130 and the dispensers 150 used for cleaning the substrate 110.

In this embodiment of the present invention, the detection system 400 includes a humidity sensor 410, positioned near the cleaning brushes 120 in the cleaning apparatus 100. The humidity sensor 410 includes sensing tips 420 for sensing the humidity present in the cleaning apparatus 100 before the cleaning process begins. Although FIG. 4 illustrates a specific embodiment of the humidity sensor 410, having the sensing tips 420 atop the humidity sensor 410, those skilled in the art understand that such sensors are available in various configurations and the present invention is broad enough to encompass any of those configurations.

Before the substrate 110 is fed into the cleaning apparatus 100, the humidity sensor 410 determines the amount of humidity present within the brush box 190. Specifically, as the dispensers 150 wet the cleaning brushes 120 with cleaning solution the ambient humidity within the brush box 190 begins to rise from the moisture of the cleaning solution. To detect the change in ambient humidity between dry and wetted cleaning brushes 120, ambient humidity reference points should be established. For example, one reference point may be the ambient humidity present when the dispensers 150 are spraying dry cleaning brushes 120, while another may be the ambient humidity present when the dispensers 150 are spraying saturated cleaning brushes 120.

This change in the ambient humidity level is detected by the sensing tips 420 of the humidity sensor 410. When compared to a reference point, the detected pH level indicates when the cleaning brushes 120 have been wetted by the cleaning solution to the degree necessary to soften the cleaning brushes 120 to a safe compressibility. In response to the detected degree of wetness, the humidity sensor 410 may generate and transmit a signal to the operator of the cleaning apparatus 100 to inform him that the cleaning brushes 120 have a sufficient degree of wetness, and thus compressibility, to clean but not damage the substrate 110 during the cleaning process. However, as with all the embodiments of the present invention, the generation and transmission of a signal is not necessary to the broad scope of the present invention.

Figure 5:
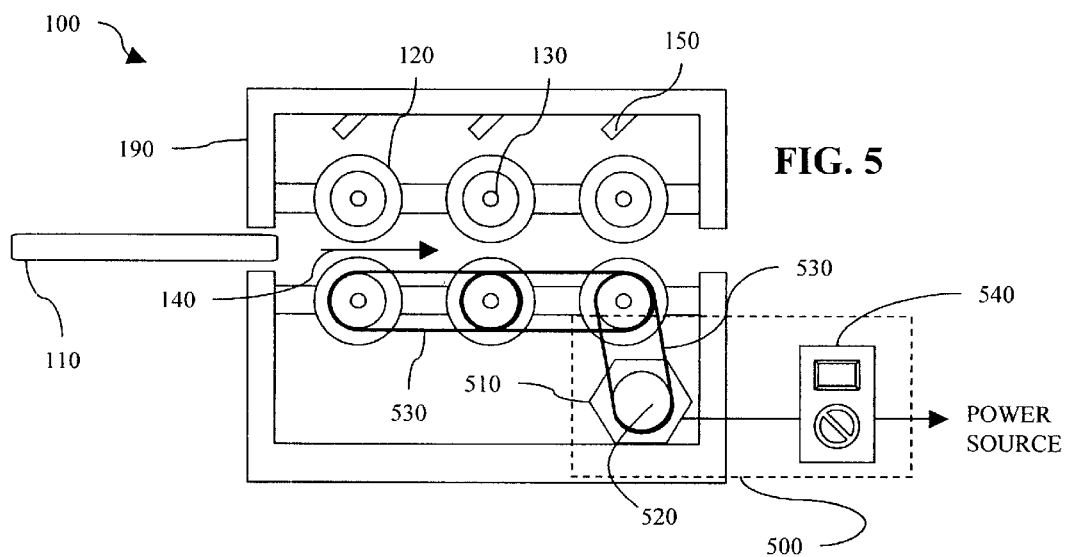
FIG. 5 illustrates a side, sectional view of the cleaning apparatus of FIG. 1 incorporating yet another embodiment of a detection system.

Turning now to FIG. 5, illustrated is a side, sectional view of the cleaning apparatus 100 of FIG. 1 incorporating yet another embodiment of a detection system 500 of the present invention. The cleaning apparatus 100 still includes a brush box 190 having the cleaning brushes 120, the shafts 130 and the dispensers 150 used for cleaning the substrate 110, as the substrate 110 is passed through the cleaning apparatus 100.

This exemplary embodiment of the detection system 500 now includes a drive motor 510 for rotating the cleaning brushes 120 during the cleaning process. Those skilled in the art understand that the cleaning apparatus 100 typically requires some type of drive motor to rotate the cleaning brushes 120, however the drive motor 510 was not illustrated in the previous embodiments for the sake of simplicity. In the detection system 500, the drive motor 510 turns multiple drive belts, collectively designated 530, with a drive pulley 520. In addition, the drive motor 510 is coupled to a power source, drawing electrical power therefrom. Interposed between the drive motor 510 and the power source is a current meter 540. The current meter 540 is coupled to the power input of the drive motor 510 to measure its load current during the cleaning process. Although other drive belts 530, pulleys or components may be required to operate the cleaning apparatus 100, those components are not essential to the present invention and have been omitted for the sake of simplicity.

When the drive motor 510 rotates the cleaning brushes 120, but before the substrate 110 is fed into the cleaning apparatus 100, a load current detected by the current meter 540 indicates the amount of work required of the drive motor 510. As the substrate 110 is fed into the cleaning apparatus 100 and begins to be compressed between opposing cleaning brushes 120, the work required of the drive motor 510 changes. More specifically, if the cleaning brushes 120 have been sufficiently wetted with cleaning solution before the substrate 110 is fed into the cleaning apparatus 100, the cleaning brushes 120 will have the amount of compressibility needed to prevent scratching or otherwise damaging the substrate 110 during cleaning. Thus, as the substrate 110 advances between opposing cleaning brushes 120 the load current of the drive motor 510 will increase as the cleaning brushes 120 compress against and clean the substrate 110. When the cleaning brushes 120 have a high degree of wetness, the increase in load current of the drive motor 510 is marginal, informing the operator that the cleaning brushes 120 are soft enough to give way to the substrate 110 and therefore not damage it during the cleaning process.

However, if the cleaning brushes 120 have a low degree of wetness before the substrate 110 is passed through the brush box 190, and thus do not have the desired compressibility, the work required by the drive motor 510 to squeeze the substrate 110 between hard cleaning brushes 120 increases proportionally to the degree of hardness. When the work of the drive motor 510 increases, its load current also increases, and this increase in load current is detected by the current sensor 540. If the current sensor 540 detects the load current has increased past a predetermined level, a signal is generated and transmitted to the operator, informing the operator that the degree of wetness of the cleaning brushes 120 is insufficient to assure no damage comes to the substrate 110 during the cleaning process. Alternatively, the a signal may be generated only when the cleaning brushes 120 have attained a high degree of wetness. As with all the embodiments of the present invention, the detection system 500 allows the operator to quickly and confidently determine whether the cleaning brushes 120 have been sufficiently wetted before a substrate 110 is cleaned, without the delays or risks associated with the approaches found in the prior art.

Figure 6:
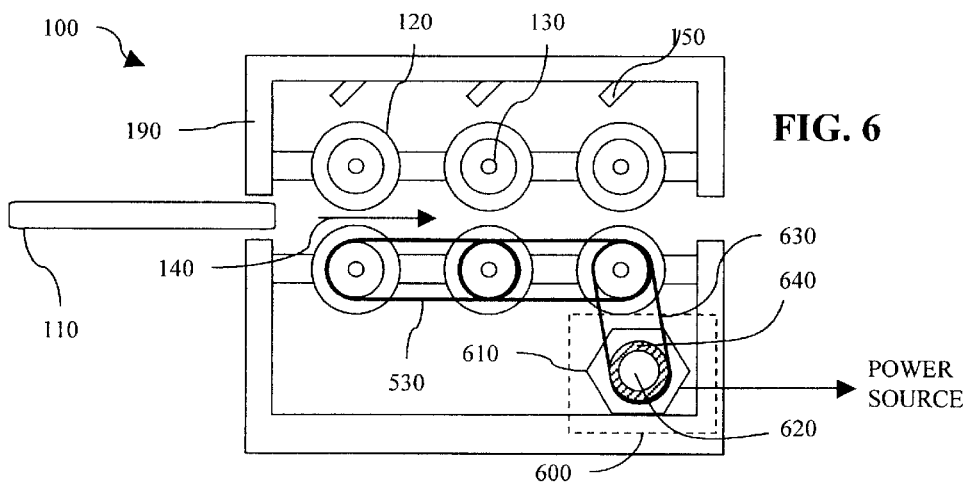
FIG. 6 illustrates a side, sectional view of the cleaning apparatus of FIG. 1 incorporating another aspect of a detection system of the present invention.

Referring now to FIG. 6, illustrated is a side, sectional view of the cleaning apparatus 100 of FIG. 1 incorporating another aspect of a detection system 600 of the present invention. Like the previous embodiments, the cleaning apparatus 100 includes the brush box 190 having multiple cleaning brushes 120, each rotating on its respective shaft 130, as well as the dispensers 150 used for wetting the cleaning brushes 120 before the substrate 110 is passed through the cleaning apparatus 100.

In addition, the detection system 600 is similar to the detection system 500 of FIG. 5 in that it also illustrates the cleaning apparatus 100 with a drive motor 610 coupled to an electrical power source. When turning, the drive motor 610 rotates a drive pulley 620 which then turns several drive belts 630. The drive belts 630 are coupled to the cleaning brushes 120, allowing the drive motor 610 to rotate the cleaning brushes 120 during the cleaning process. As before, although other drive belts 630 or pulleys may be required for operation of the cleaning apparatus 100, those components are not essential to the present invention and thus have been omitted for the sake of simplicity.

The drive motor 610 now also includes a torque sensor 640, coupled to the drive pulley 620 and around which one of the drive belts 630 is located. As the drive motor 610 uses the drive pulley 620 to turn the drive belts 630, the torque sensor 640 detects the amount of torque required for the drive motor 610 to turn the cleaning brushes 120 during the cleaning process. Of course, coupling the torque sensor 640 to the drive pulley 620 is only an exemplary embodiment of the present invention. The torque sensor 640 may also be positioned in other locations, for example on one of the cleaning brushes 120 itself.

If the cleaning brushes 120 are sufficiently wetted, and thus have sufficient compressibility, the increase in torque when the substrate 110 passes between opposing cleaning brushes 120 is only marginally increased from when no substrate 110 is present. The marginal increase detected by the torque sensor 640 informs the operator that the degree of wetness of the cleaning brushes 120 is such that the cleaning brushes 120 will compress against but give way to and not damage the substrate 110 as it passes through the brush box 190 during the cleaning process.

However, as before, if the cleaning brushes 120 have not been sufficiently wetted before the substrate 110 is cleaned, the cleaning brushes 120 will not have the necessary compressibility needed to clean the substrate 110 without the risk of damaging it in the process. Thus, as the substrate 110 begins to pass between the first pair opposing cleaning brushes 120, the cleaning brushes 120 do not compress and give way to the substrate 110 as easily, and the work required by the drive motor 610 to squeeze the substrate 110 between the hard cleaning brushes 120 increases. When the harder cleaning brushes 120 resist passage of the substrate 110 therebetween, the torque required by the drive motor 610 to turn the cleaning brushes 120, and consequently the drive pulley 620, also increases. Thus, the increased torque is detected by the torque sensor 640, and a signal is generated and transmitted to the operator, informing the operator that the degree of wetness of the cleaning brushes 120 is insufficient to allow the substrate 110 to pass through the cleaning apparatus 100 without some risk of damage occurring during the cleaning process. As such, the torque detection system 600 again allows an operator to easily determine whether the cleaning brushes 120 have been sufficiently wetted before a substrate 110 is cleaned, without the delays or expense found in the prior art.

Figure 7:
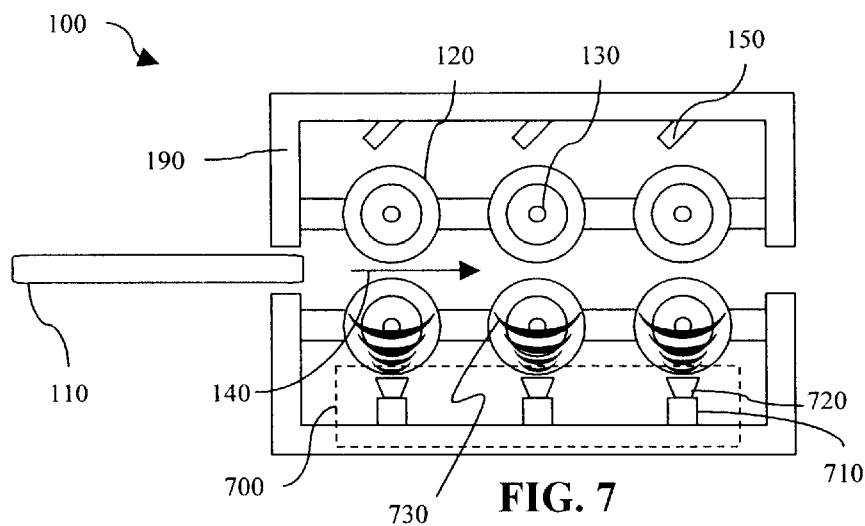
FIG. 7 illustrates a side, sectional view of the cleaning apparatus of FIG. 1 incorporating still a further embodiment of a detection system.

Looking now at FIG. 7, illustrated is a side, sectional view of the cleaning apparatus 100 of FIG. 1 incorporating still a further embodiment of a detection system 700 of the present invention. The cleaning apparatus 100 still includes the brush box 190, cleaning brushes 120, shafts 130 and the dispensers 150 collectively used for cleaning the substrate 110.

In this embodiment of the present invention, the detection system 700 includes acoustic sensors, one of which is designated 710. The acoustic sensors 710 generate and transmit acoustic waves 730 to at least one of the cleaning brushes 120 via wave generators, one of which is designated 720. The acoustic waves 730 contact and penetrate the cleaning brush 120, bouncing and oscillating within the material of the cleaning brush 120. Depending on the overall composition of the cleaning brush 120, a portion of the acoustic waves 730 will return to and be absorbed by the acoustic sensor 710. The characteristics of the returned portion of the acoustic waves 730, such as frequency and wavelength, will then be indicative of the composition of the material of the cleaning brush 120.

When the dispensers 150 are first activated and the cleaning brushes 120 have not yet attained a high degree of wetness, the acoustic waves 730 generated by the wave generators 720 oscillate and return to the acoustic sensors 710 with a frequency and wavelength indicative of only the dry or partially moistened cleaning brush 120 material. In this case, the acoustic sensors 710 would inform the operator that the cleaning brushes 120 have not yet attained a high degree of wetness. Thus, cleaning the substrate 110 with the cleaning brushes 120 in this condition may result in scratching or otherwise damaging the substrate 110.

On the other hand, if the cleaning brushes 120 have been sufficiently wetted with the solution, a portion of the acoustic waves 730 transmitted through the cleaning brushes 120 would return to the acoustic sensors 710 with a frequency and wavelength indicative of a high degree of wetness of the cleaning brush 120 material. Specifically, the degree of wetness is determined from the level of saturation of the cleaning brush 120 material with a cleaning solution. Once the acoustic sensors 710 determine a high degree of wetness, the operator would be informed, perhaps with the computer system 330 of FIG. 3, that the cleaning brushes 120 have attained a predetermined degree of wetness. As a result, the predetermined degree of wetness may then be interpreted to mean the cleaning brushes 120 have the necessary compressibility to allow the substrate 110 to be cleaned with little or no damage to the substrate 110 surface. As before, the detection system 700 embodied in FIG. 7 provides the operator with a degree of certainty in determining the risk of damaging the substrate 110 during the cleaning process, before the process even begins, without the substantial delays or risks to technicians found in the prior art approaches.

In another aspect of the embodiment illustrated in FIG. 7, the detection system 700 may instead use electrical current, rather than acoustic waves, to detect wetness. Specifically, the sensors 710 would transmit an electrical current through the cleaning brush 120 in order to determine the resistance of the cleaning brush 120 material. As the wetness of the cleaning brush 120 increases, the electrical current more easily conducts through the cleaning brush 120 material. As a result, the resistance detected decreases. This decrease in resistance informs the operator that the cleaning brushes 120 in the brush box 190 are thoroughly wetted before the substrate 110 is fed through. In this embodiment, like the others, the advantages over the prior art detection techniques are retained.

Figure 8:
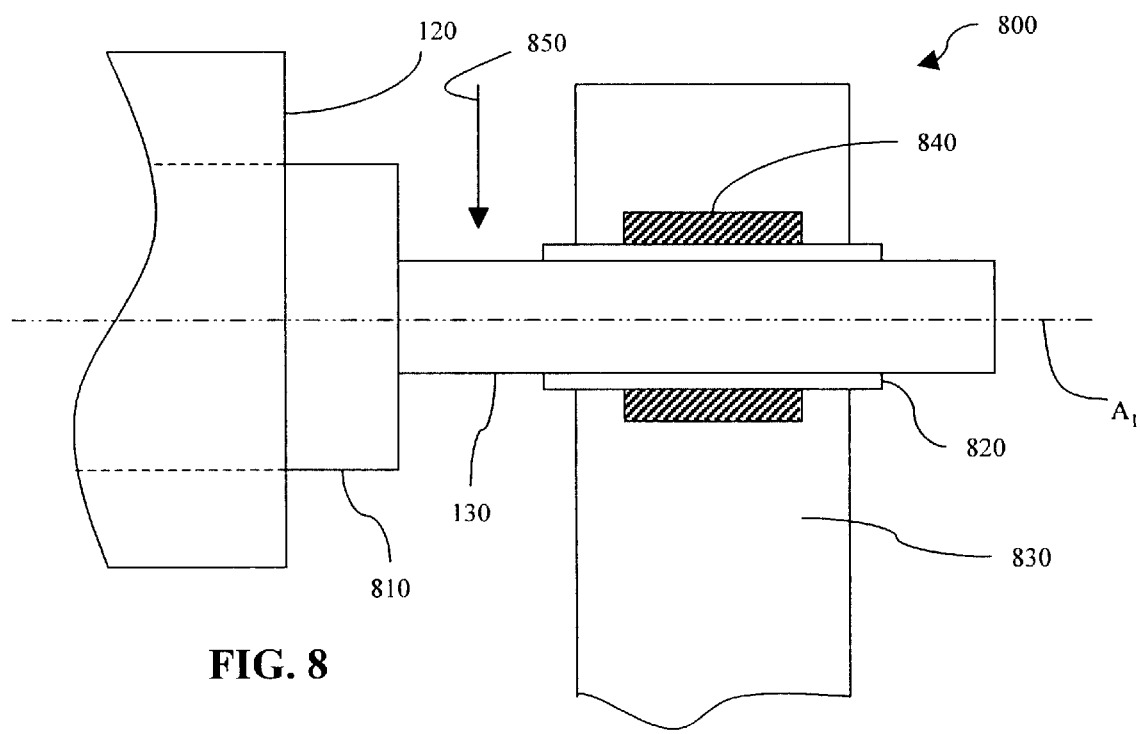
FIG. 8 illustrates a close-up, sectional view of one end of a cleaning brush 120 assembly illustrated in FIGS. 1–7 for use with another embodiment of a detection system 800 of the present invention.

Turning to FIG. 8, illustrated is a close-up, sectional view of one end of a cleaning brush 120 assembly illustrated in FIGS. 1–7 for use with another embodiment of a detection system 800 of the present invention. The assembly includes the cleaning brush 120, an arbor 810 on which the cleaning brush 120 is mounted, and the shaft 130 on which the cleaning brush 120 assembly rotates.

This advantageous embodiment of the detection system 800 of the present invention further includes a roller bearing 820 positioned about the shaft 130, and a brush mount 830 in which the shaft 130 and roller bearing 820 are mounted. The brush mount 830 is held securely within the brush box 190 and holds the cleaning brush 120 in position while allowing it to rotate within the roller bearing 820 about a longitudinal axis $A_1$. The detection system 800 still further includes a pressure sensor 840 located within the brush mount 830 and positioned proximate the roller bearing 820. The pressure sensor 840 is preferably positioned outside the roller bearing 820 so as not to interfere with the rotation of the shaft 130, however the present invention is no so limited. The detection system 800 functions as follows.

As before, the cleaning brush 120 is wetted with a cleaning solution as it rotates on the shaft 130 prior to feeding the substrate 110 through the cleaning apparatus 100. If the cleaning brush 120 has a sufficient degree of wetness, it also has at least the desired amount of compressibility. This amount of compressibility allows the substrate 110 to pass between opposing cleaning brushes 120 with the thoroughly wetted material of the cleaning brushes 120 giving way to, and therefore not damaging, the substrate 110. With the material of the cleaning brushes 120 compressing, the arbor 810 and the shaft 130 are only slightly forced in an outward direction 850 away from the substrate 110 as the substrate 110 passes between opposing cleaning brushes 120. Since the arbor 810, and consequently the shaft 130, are only marginally forced away from the substrate 110 as the cleaning brush 120 material gives way to the substrate 110, the pressure sensor 840 does not detect a significant change in the pressure applied to the roller bearing 820 by the shaft 130. When the pressure sensor 840 does not detect a significant change in pressure, a signal to the operator is not generated indicating that the cleaning brushes 120 have a high degree of wetness, and thus have at least the compressibility necessary to clean the substrate 110 with little or no risk of damaging it in the process.

When the cleaning brushes 120 have not been sufficiently wetted before the substrate 110 is cleaned, the cleaning brushes 120 do not have the necessary compressibility. Without the desired compressibility, as the substrate 110 begins to pass between the first set of opposing cleaning brushes 120, the material of the cleaning brushes 120 does not easily give way to the substrate 110. Since the cleaning brush 120 material does not easily give way to the substrate 110, pressure is applied in the outward direction 850 away from the substrate 110 and against the arbor 810 and the shaft 130 via the material. Consequently, the pressure applied to the pressure sensor 840 by the shaft 130 indicates to the operator that the cleaning brushes 120 do not have a high degree of wetness. With this notification, the operator may stop the cleaning process to prevent any damage from coming to the substrate 110. Moreover, the degree of wetness of the cleaning brushes 120 may be determined with certainty without the deficiencies found in the approaches of the prior art.

Figure 9:
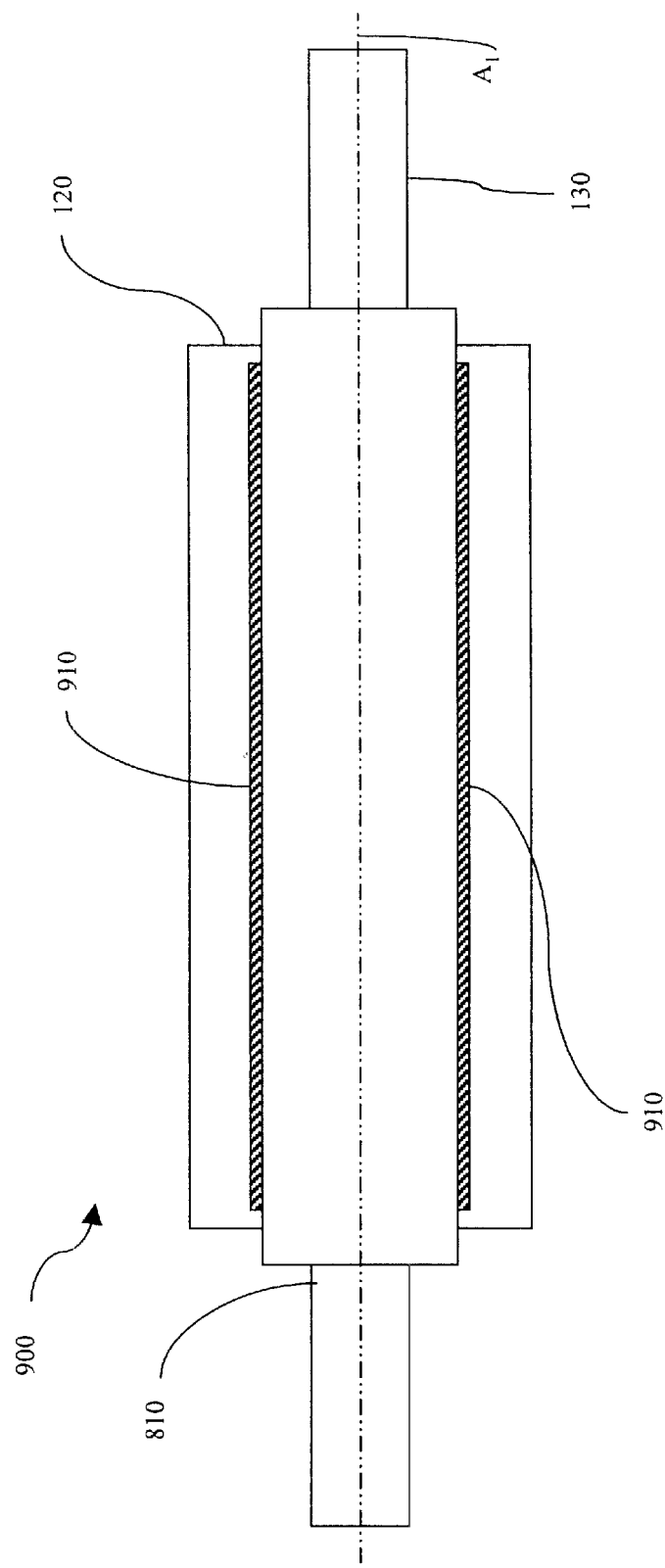
FIG. 9 illustrates a side, sectional view of the cleaning brush assembly of FIGS. 1–8 incorporating yet another embodiment of a detection system of the present invention.

Referring finally to FIG. 9, illustrated is a side, sectional view of the cleaning brush 120 assembly illustrated in of FIG. 8 incorporating yet another embodiment of a detection system 900 of the present invention. The assembly includes the cleaning brush 120, the arbor 810 on which the cleaning brush 120 is mounted, and the shaft 130 on which the cleaning brush 120 assembly rotates. The cleaning brush 120 still rotates about a longitudinal axis $A_1$ prior to and during the cleaning process.

In this embodiment of the present invention, the detection system 900 further includes a pressure sensor 910 mounted about the arbor 810, along a longitudinal length of the cleaning brush 120 assembly. Thus, the pressure sensor 910 is positioned directly between the material of the cleaning brush 120 and the arbor 810 on which it is mounted. The detection system 900 illustrated in FIG. 9 functions in a similar manner to the detection system 800 of FIG. 8, as discussed below.

The cleaning brush 120 is wetted with a cleaning solution as it rotates on the shaft 130 prior to feeding the substrate 110 through the cleaning apparatus 100. If the cleaning brush 120 has a sufficient degree of wetness, it also has at least the desired amount of compressibility, allowing the substrate 110 to pass between opposing cleaning brushes 120 with the thoroughly wetted material of the cleaning brushes 120 giving way to the substrate 110. With this high degree of wetness, the material of the cleaning brushes 120 compresses and gives way to the substrate 110, applying very little force against the arbor 810. Since only a marginal force is applied against the arbor 810, and consequently the pressure sensor 910, the pressure sensor 910 does not transmit a signal indicating a low degree of wetness of the cleaning brush 120. As a result, the operator may clean the substrate 110 with little or no risk of damage to it in the process.

In contrast, if the degree of wetness of the cleaning brush 120 is low, the material of the cleaning brush 120 only compresses a little, or not at all, in response to the substrate 110 passing between opposing cleaning brushes 120. By only marginally compressing as the substrate 110 passes between, the substrate 110 causes the cleaning brush 120 material to exert a greater force on the arbor 810, and consequently the pressure sensor 910. The pressure sensor 910 detects this increase in force, determining that the degree of wetness of the cleaning brush 120 is insufficient to safely clean the surfaces of the substrate 110. Thus, as before, the operator will be informed that the cleaning process may cause damage to the substrate 110 if the cleaning brushes 120 are not permitted further time to reach a higher degree of wetness before the substrate 110 is cleaned. In addition, the pressure sensor 910 determines this insufficient wetness without the deficiencies and risks associated with the approaches found in the prior art.

In sum, using any embodiment of a wetness detection system according to the present invention, the operator of a semiconductor wafer cleaning apparatus may more easily and accurately determine whether the cleaning brushes of the cleaning apparatus have attained a degree of wetness sufficient to clean a wafer without a significant risk of damaging the wafer during the cleaning process. For example, gone are the unnecessary delays of the cleaning apparatus running empty for longer than is required to saturate the cleaning brushes simply because an operator cannot be certain that the cleaning brushes are sufficiently wetted before a wafer is cleaned. Also, wetness of the cleaning brushes is more easily determined by detecting the degree of wetness without the delay of opening the brush box to visually inspect the cleaning brushes. Perhaps more importantly, the risk of chemical burns to technicians, caused by exposure to cleaning solutions in the brush box, is eliminated since the brush box no longer needs to be opened to determine the degree of brush wetness. In addition, a window in the brush box, which typically allows light rays to negatively affect the cleaning solutions used during the cleaning process, need not be used or even installed.

Those skilled in the art will understand that these and other deficiencies associated with the prior art are overcome with the wetness detection system, and associated method, of the present invention. Additionally, although the present invention has been described in detail, referring to several specific embodiments, those skilled in the art should understand that they can make various changes, substitutions and alterations herein without departing from the spirit and scope of the present invention in its broadest form.

What is claimed is:

1. A wafer cleaning apparatus comprising:
   cleaning brushes mounted within a brush box;
   a dispenser within the brush box for dispensing cleaning solution; and
   a sensor within the brush box, the sensor located proximate an outer surface of at least one of the cleaning brushes and configured to detect a degree of wetness of the at least one of the cleaning brushes.

2. The wafer cleaning apparatus as recited in claim 1 wherein the cleaning brushes comprise polyvinyl alcohol and wherein the sensor is a compressibility sensor positionable against the at least one of the cleaning brushes and configured to determine a degree of compressibility of the at least one of the cleaning brushes, the amount of compressibility being indicative of a degree of wetness of the at least one of the cleaning brushes.

3. The wafer cleaning apparatus as recited in claim 1 wherein the sensor is an optical sensor configured to detect an amount of reflectivity from the at least one of the cleaning brushes, the amount of reflectivity being indicative of a degree of wetness of the at least one of the cleaning brushes.

4. The wafer cleaning apparatus as recited in claim 1 wherein the sensor is an acoustic sensor configured to transmit an acoustic wave through the at least one of the cleaning brushes, an amount of transmission of the acoustic wave being indicative of a degree of wetness of the at least one of the cleaning brushes.

5. The wafer cleaning apparatus as recited in claim 1 wherein the sensor is a pH sensor configured to detect a pH level of the at least one cleaning brush, the pH level being indicative of a degree of wetness of the at least one cleaning brush.

6. The wafer cleaning apparatus as recited in claim 1 wherein the sensor is a humidity sensor configured to detect an ambient humidity of the brush box, the ambient humidity being indicative of a degree of wetness of the at least one cleaning brush.

7. The wafer cleaning apparatus as recited in claim 1 wherein the cleaning brushes are opposing one another and wherein the sensor is a pressure sensor coupled to an arbor of at least one of the opposing cleaning brushes, the pressure sensor configured to detect a pressure exerted against the at least one of the opposing cleaning brushes when a wafer is inserted therebetween, the pressure being indicative of a degree of wetness of the at least one of the opposing cleaning brushes.

* * * * *